United States Patent [19]

Fuchs et al.

[11] 4,297,371
[45] Oct. 27, 1981

[54] COMBATING PESTS WITH (±)-TRANS-3-(E/Z-2-CHLORO-2-(4-CHLOROPHENYL)-VINYL)-2,2-DIMETHYL-CYCLOPROPANECARBOXYLIC ACID (±)-(α-CYANO-3-PHENOXY-4-FLUORO-BENZYL) ESTER AND THE INDIVIDUAL E- AND Z-ISOMERS

[75] Inventors: Rainer Fuchs; Bernd Gallenkamp; Wilhelm Stendel, all of Wuppertal, Fed. Rep. of Germany

[73] Assignee: Bayer Aktiengesellschaft, Leverkusen, Fed. Rep. of Germany

[21] Appl. No.: 182,356

[22] Filed: Aug. 29, 1980

[30] Foreign Application Priority Data

Sep. 12, 1979 [DE] Fed. Rep. of Germany ....... 2936864

[51] Int. Cl.$^3$ ..................... A01N 53/00; C07C 61/35; C07C 69/743; C07C 121/75
[52] U.S. Cl. ........................ 424/304; 260/465 D; 260/544 P; 560/8; 562/405
[58] Field of Search ...................... 260/465 D, 544 P; 424/304; 560/8; 562/405

[56] References Cited

FOREIGN PATENT DOCUMENTS 2730515 1/1979 Fed. Rep. of Germany .

*Primary Examiner*—Dolph H. Torrence
*Attorney, Agent, or Firm*—Sprung, Felfe, Horn, Lynch & Kramer

[57] ABSTRACT

Combating ectoparasites with the substantially pure isomer mixture (±)-trans-3-(E/Z-2-Chloro-2-(4-chlorophenyl)-vinyl)-2,2-dimethyl-cyclopropanecarboxylic acid (±)-(α-cyano-3-phenoxy-4-fluoro-benzyl) ester or the individual E- and Z-isomers of the formula

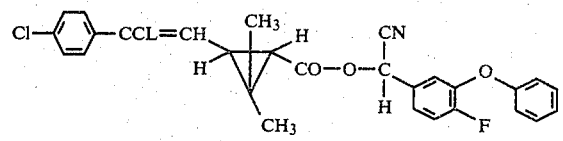

The intermediate free acids, acid chlorides and esters thereof are also shown.

10 Claims, No Drawings

COMBATING PESTS WITH (±)-TRANS-3-(E/Z-2-CHLORO-2-(4-CHLORO-PHENYL)-VINYL)-2,2-DIMETHYL-CYCLO-PROPANECARBOXYLIC ACID (±)-(α-CYANO-3-PHENOXY-4-FLUORO-BENZYL) ESTER AND THE INDIVIDUAL E- AND Z-ISOMERS

The invention relates to the new E/Z isomer mixture of (±)-trans-3-(E/Z-2-chloro-2-(4-chlorophenyl)-vinyl)-2,2-dimethyl-cyclopropanecarboxylic acid (±)-(α-cyano-3-phenoxy-4-fluoro-benzyl)ester and the individual E- and Z-isomers of the mixture, to a process for the preparation of these compounds and to their use as ectoparasiticides.

It is already known that mixtures of the (±)-cis- and (±)-trans- forms of 3-(E/Z-2-chloro-2-(4-chloro-phenyl)-vinyl)-2,2-dimethyl-cyclopropane-1-carboxylic acid (±)-(α-cyano-3-phenoxy-4-fluoro-benzyl)ester have an insecticidal and acaricidal action, U.S. Ser. No. 916,163, filed June 16, 1978.

The present invention now provides the E/Z-isomer mixture of (±)-trans-3-(2-chloro-2-(4-chloro-phenyl)-vinyl)-2,2-dimethyl-cyclopropane-1-carboxylic acid (±)-(α-cyano-3-phenoxy-4-fluoro-benzyl)ester, of the formula

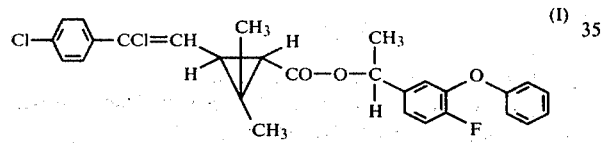

and the E-isomer of the formula

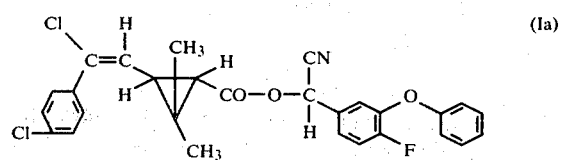

and the Z-isomer of the formula

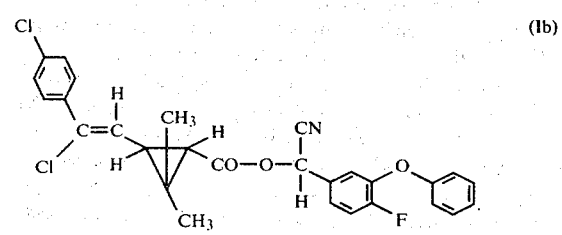

The invention also provides a process for the preparation of the compounds of the formulae (I), (Ia) and (Ib) in which an E/Z-isomer mixture of (±)-trans-3-(2-chloro-2-(4-chloro-phenyl)-vinyl)-2,2-dimethyl-cyclopropane-1-carboxylic acid chloride of the formula

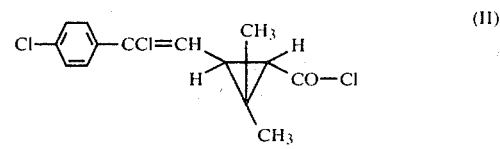

or the E-isomer of the formula

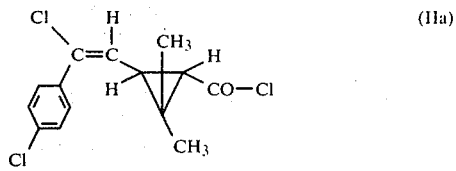

or the Z-isomer of the formula

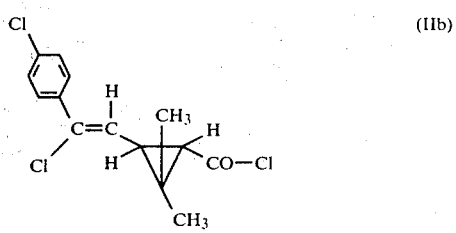

is reacted with 3-phenoxy-4-fluoro-benzaldehyde, of the formula

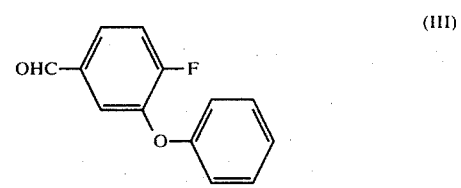

in the presence of at least an equimolar amount of an alkali metal cyanide, if appropriate in the presence of a catalyst and if appropriate using a diluent, at a temperature between 0° and 100° C.

A further possible method for the preparation of the E-isomer of the formula (Ia) and of the Z-isomer of the formula (Ib) consists in resolving the E/Z-isomer mixture of (±)-trans-3-(2-chloro-2-(4-chlorophenyl)-vinyl)-2,2-dimethyl-cyclopropane-1-carboxylic acid (±)-(α-cyano-3-phenoxy-4-fluoro-benzyl)ester of the formula (I) into the individual components by methods which are in themselves known.

The new compounds of the formulae (I), (Ia) and (Ib) are distinguished by a high insecticidal and acaricidal activity.

Surprisingly, the new compounds exhibit a considerably more powerful insecticidal and acaricidal action, and in particular ectoparasiticidal action, than the isomer mixtures of 3-(2-chloro-2-(4-chlorophenyl)-vinyl)-2,2-dimethyl-cyclopropane-1-carboxylic acid (α-cyano-3-phenoxy-4-fluoro-benzyl)ester which are known from the state of the art.

The reaction which proceeds in the preparation of the E/Z-isomer mixture of the formula (I) can be outlined by the following equation:

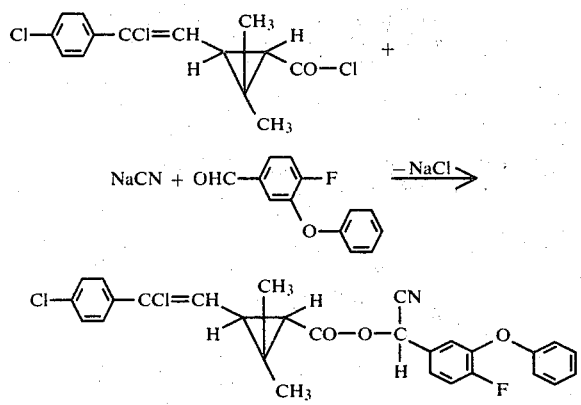

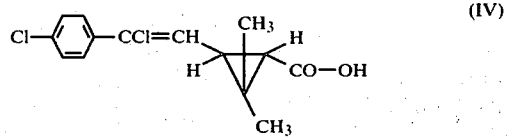

The acid chlorides of the formulae (II), (IIa) and (IIb) to be used as starting substances have not hitherto been described in the literature. These new compounds are obtained when the E/Z-isomer mixture of (±)-trans-3-(2-chloro-2-(4-chloro-phenyl)-vinyl)-2,2-dimethyl-cyclopropane-1-carboxylic acid, of the formula

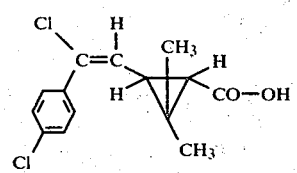 (IV)

or the E-isomer of the formula

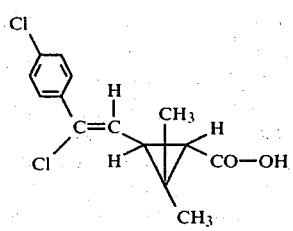 (IVa)

or the Z-isomer of the formula

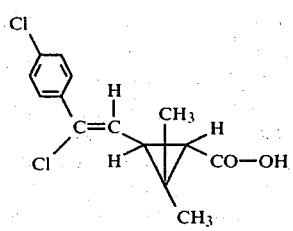 (IVb)

is reacted with a chlorinating agent, for example thionyl chloride, if appropriate in the presence of a diluent, for example carbon tetrachloride, at a temperature between 10° and 100° C.

The acids of the formulae (IV), (IVa) and (IVb) have not hitherto been described in the literature. (±)-trans-3-(E/Z-2-chloro-2-(4-chloro-phenyl)-vinyl)-2,2-dimethyl-cyclopropane-1-carboxylic acid of the formula (IV) is obtained by saponifying corresponding alkyl esters of the general formula

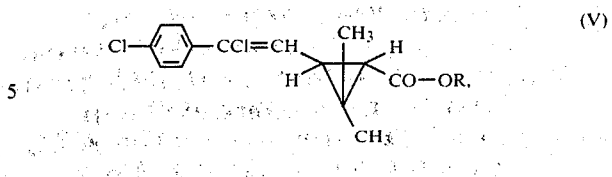 (V)

in which R represents $C_1$–$C_4$-alkyl, by customary methods, for example by heating the esters with alkali metal hydroxide solutions, for example aqueous alcoholic sodium hydroxide solution, to a temperature between 50° and 100° C. For working up, the alcohol is distilled off, if appropriate, and the product is extracted with a water-immiscible solvent, for example methylene chloride, and the extraction agent is distilled off under reduced pressure.

Examples of the esters of the formula (V) which may be mentioned are: (±)-trans-3-(E/Z-2-chloro-2-(4-chloro-phenyl)-vinyl)-cyclopropane-1-carboxylic acid methyl ester, ethyl ester, n-propyl ester, iso-propyl ester, n-butyl ester, iso-butyl ester, sec.-butyl ester and tert.-butyl ester.

The esters of the formula (V) have not hitherto been described in the literature. They are obtained by a process in which (±)-trans-3-formyl-2,2-dimethyl-cyclopropane-1-carboxylic acid esters of the general formula

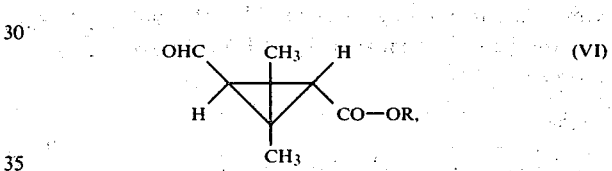 (VI)

in which R represents $C_1$–$C_4$-alkyl, are reacted with 4-chloro-α-chloro-benzyl-phosphonic acid esters of the general formula

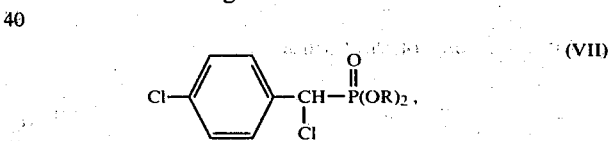 (VII)

in which R represents $C_1$–$C_4$-alkyl, in the presence of a base, for example sodium methylate, if appropriate in the presence of a diluent, for example ethanol and/or tetrahydrofuran, at a temperature between −10° and +50° C. For working up, the mixture is diluted with water and extracted with a water-immiscible solvent, for example methylene chloride. The extracts are dried and filtered and the solvent is distilled off from the filtrate under reduced pressure.

Esters of the formula (VI) are already known (see DE-OS (German Published Specification) No. 2,615,160). Examples which may be mentioned are: (±)-trans-3-formyl-2,2-dimethyl-cyclopropane-1-carboxylic acid methyl ester, ethyl ester, n-propyl ester, iso-propyl ester, n-butyl ester, iso-butyl ester, sec.-butyl ester and tert.-butyl ester.

The preparation of 4-chloro-α-chloro-benzyl-phosphonic acid esters of the formula (VII) is the subject of U.S. Ser. No. 45,473, filed June 4, 1979.

These compounds are obtained according to the following equation, starting from 4-chloro-benzaldehyde, which is known:

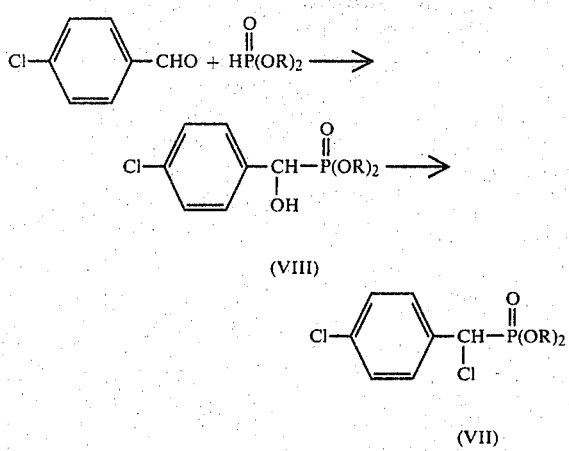

(VIII)

(VII)

4-Chloro-α-hydroxy-benzyl-phosphonic acid esters of the formula (VIII) are obtained by reacting 4-chlorobenzaldehyde with phosphorous acid esters, for example with phosphorous diethyl ester, if appropriate in the presence of a catalyst, for example triethylamine, at a temperature between 20° and 100° C. The resulting esters can be converted into the 4-chloro-α-chlorobenzyl-phosphonic acid esters of the formula (VII) by reaction with a chlorinating agent, for example with thionyl chloride, at a temperature between 20° and 100° C.

Examples of the compounds of the formula (VII) which may be mentioned are: 4-chloro-α-chloro-benzylphosphonic acid dimethyl ester, diethyl ester, diisopropyl ester and di-sec.-butyl ester.

3-Phenoxy-4-fluoro-benzaldehyde of the formula (III), which is to be employed as a starting compound for the preparation of the new compounds of the formulae (I), (Ia) and (Ib), is already known U.S. Ser. No. 100,583, filed Dec. 5, 1979.

Alkali metal cyanides which are to be used for the preparation of the new compounds of the formulae (I), (Ia) and (Ib) are preferably sodium cyanide and potassium cyanide.

The process for the preparation of the new compounds of the formulae (I), (Ia) and (Ib) is preferably carried out using a diluent. Possible diluents are virtually any of the inert organic solvents. These include, as preferences, aliphatic and aromatic, optionally chlorinated hydrocarbons, such as pentane, hexane, heptane, cyclohexane, benzene, toluene, xylene, methylene chloride, chloroform, carbon tetrachloride, chlorobenzene and o-dichlorobenzene; ethers, such as diethyl ether and dibutyl ether, tetrahydrofuran and dioxane; ketones, such as acetone, methyl ethyl ketone, methyl iso-propyl ketone and methyl isobutyl ketone; and nitriles, such as acetonitrile and proponitrile.

Of the above-mentioned solvents, those which are water-immiscible are preferably used, in combination with water as a second solvent component, that is to say the process is carried out in a two-phase medium.

In this case, compounds which are usually used as auxiliaries for the phase transfer of reactants in reactions in multi-phase media can be employed as catalysts. Tetraalkyl-and trialkyl-aralkyl-ammonium salts, for example tetrabutylammonium bromide, methyl trioctylammonium chloride and trimethylbenzylammonium bisulphate, may be mentioned in particular.

The reaction temperature is in general kept between 0° and 100° C., preferably between 10° and 50° C. The preparation process is usually carried out under normal pressure.

The starting substances are usually employed in equimolar amounts for carrying out the process according to the invention. An excess of one or the other of the reactants brings no substantial advantages. The reaction is in general carried out in a suitable diluent, if appropriate in the presence of a catalyst, and the reaction mixture is stirred at the required temperature for several hours. Thereafter, an organic solvent, for example toluene, is added and the organic phase is worked up in the customary manner by washing and drying, and distilling off the solvent.

The new compounds of the formula (I), (Ia) and (Ib) are obtained in the form of oils and cannot be distilled without decomposition, but they can be freed from the last volatile constituents by so-called "incipient distillation," that is to say by prolonged heating to moderately elevated temperatures under reduced pressure, and purified in this manner. They are characterized by their $^1$H-NMR spectrum.

E/Z-isomer mixtures of (±)-trans-3-(E/Z-2-chloro-2-(4-chloro-phenyl)-vinyl)-2,2-dimethyl-cyclopropane-1-carboxylic acid of the formula (IV) above can be resolved by dissolving the E/Z-isomer mixture of the acid (IV) in a water-immiscible solvent, for example methylene chloride, converting the acid into the salt by adding 0.001 to 1, preferably 0.1 to 1, equivalent of a base, for example aqueous sodium hydroxide solution, in X steps, X representing a number between 1 and ∞, ∞ denoting a continuous procedure, but preferably representing 2 to 100, and extracting the salt, after each addition of base, with water in X steps, acidifying the individual aqueous fractions with a mineral acid, for example hydrochloric acid, and extracting them with a water-immiscible solvent, for example methylene chloride, working up each individual extract by customary methods, for example by drying and filtering and distilling off the solvent from the filtrate, and recrystallizing the fractions, in which, according to analysis by NMR spectroscopy, one of the isomers of the formula (IVa) or (IVb) predominates, from an organic solvent, preferably a hydrocarbon with 5 to 10 carbon atoms.

E/Z-isomer mixtures of (±)-trans-3-(E/Z-2-chloro-2-(4-chloro-phenyl)-vinyl)-2,2-dimethyl-cyclopropane-1-carboxylic acid of the formula (IV) can be resolved by dissolving the E/Z-isomer mixture of the acid (IV) in an aqueous alkali metal hydroxide solution, for example sodium hydroxide solution, which contains exactly one base equivalent, producing the acid again by adding 0.001 to 1, preferably 0.1 to 1, equivalent of a mineral acid in X steps, X representing a number between 1 and ∞, ∞ denoting a continuous procedure, but preferably being between 2 and 100, extracting the acid, after each addition of acid, with a water-immiscible organic solvent, for example methylene chloride, working up each individual extract by customary methods, for example by drying and filtering and distilling off the solvent from the filtrate, and recrystallizing the fractions, in which, according to analysis by NMR spectroscopy, one of the isomers of the formula (IVa) or (IVb) predominates, from an organic solvent, preferably a hydrocarbon with 5 to 10 carbon atoms.

The active compounds according to the invention exhibit a powerful and rapidly effective ectoparasiticidal (insecticidal and acaricidal) action, in particular against acarids which, as animal ectoparasites, infest domesticated animals, such as cattle, sheep and rabbits, coupled with a low toxicity to warm-blooded animals. They are thus very particularly suitable for combating ectoparasites from the class of acarids.

The active compounds according to the invention can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, and very fine capsules in polymeric substances.

These formulations may be produced in known manner, for example by mixing the active compounds with extenders, that is to say liquid or liquefied gaseous or solid diluents or carriers, optionally with the use of surface active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

Formulations of the active compound combinations according to the invention are prepared in a manner which is in itself known, by mixing together the individual components, in the individually required proportions, the sequence of the addition of active compounds and additives and the formulation auxiliaries in general being of no particular importance.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating insects or acarids which comprises applying to the insects or acarids, or to a habitat thereof, a compound of the present invention alone or in the form of a composition containing as active ingredient a compound of the present invention in admixture with a diluent or carrier.

The present invention also provides a method of freeing or protecting domesticated animals from ectoparasites which comprises applying to said animals a compound according to the present invention, in admixture with a diluent or carrier.

The present invention further provides domesticated animals whenever freed or protected from ectoparasites by the application to said animals of a compound according to the present invention, in admixture with a diluent or carrier.

PREPARATIVE EXAMPLES

EXAMPLE 1

(a) The ester of the formula (V) to be used as the starting compound could be prepared as follows:

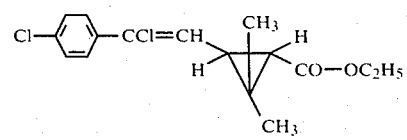

2.53 g (0.11 mol) of sodium were dissolved in portions in 50 ml of ethanol. When all the sodium has dissolved, 150 ml of tetrahydrofuran (anhydrous) were added, and 29.7 g (0.1 mol) of 4-chloro-α-chlorobenzyl-phosphonic acid diethyl ester, dissolved in 30 ml of anhydrous tetrahydrofuran, were added dropwise at 0° C., while stirring. After the mixture has been subsequently stirred for a further 2 hours at 0°–5° C., 17 g (0.1 mol) of trans-2,2-dimethyl-3-formyl-cyclopropane-carboxylic acid ethyl ester, dissolved in 30 ml of anhydrous tetrahydrofuran, were added dropwise at 0° C., while stirring. The mixture was then subsequently stirred for a further 12 hours at 20°–25° C. 500 ml of water were then added to the reaction mixture and the mixture was extracted twice with 300 ml of methylene chloride. The organic phases were separated off and dried over magnesium sulphate, the solvent was distilled off under a waterpump vacuum and the residue was distilled in vacuo. 23.2 g (74.1% of theory) of (±)-trans-3-(E/Z-2-chloro-2-(4-chloro-phenyl)-vinyl)-2,2-dimethyl-cyclopropanecarboxylic acid ethyl ester were obtained as a yellow oil with a boiling point of 155°–165° C./1 mm Hg.

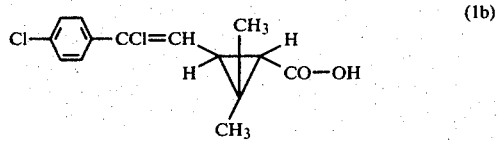

(1b)

From Example 1(a) hereinabove 22.2 g (0.071 mol) of (±)-trans-3-(E/Z-2-chloro-2-(4-chloro-phenyl)-vinyl)-2,2-dimethyl-cyclopropanecarboxylic acid ethyl ester were dissolved in 100 ml of ethanol, a solution of 5.7 g of sodium hydroxide in 100 ml of water was then added and the mixture was heated to the reflux temperature for 4 hours, while stirring. The ethanol was then distilled off under a waterpump vacuum, the residue was taken up in 300 ml of warm water and the aqueous mixture was extracted once with 300 ml of methylene chloride. The aqueous phase was separated off, acidified with concentrated hydrochloric acid and then extracted with 2×300 ml of methylene chloride. The organic phases were separated off, dried over magnesium sulphate and the solvent was distilled off under a waterpump vacuum. Last residues of solvent were removed by brief incipient distillation at a bath temperature of 60° C./2 mm Hg. 15.5 g (76.6% of theory) of (±)-trans-3-(E/Z-2-chloro-2-(4-chloro-phenyl)-vinyl)-2,2-dimethyl-cyclopropanecarboxylic acid were obtained as a viscous oil, which crystallized after some time. When recrystallized from acetonitrile, the product melted at 120°–132° C.

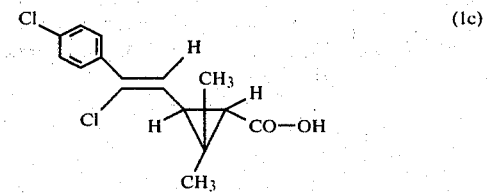

(1c)

130.2 g (0.4568 mol) of (±)-trans-(E/Z-2-chloro-2-(4-chloro-phenyl)-vinyl)-2,2-dimethyl-cyclopropane-carboxylic acid with an E/Z ratio of 60/40 were suspended in 500 ml of water and were converted into the sodium salt by adding 18.27 g (0.4568 mol) of sodium hydroxide, dissolved in 100 ml of water, while stirring. A layer of 100 ml of methylene chloride was introduced underneath the aqueous salt solution, and 0.04568 mol of hydrogen chloride was added in the form of a 37% strength aqueous solution, while stirring vigorously. The mixture was subsequently stirred for a further 5 minutes and the methylene chloride phase was then separated off. The acidification and separation were repeated a total of 9 more times in the same manner. The 10 methylene chloride phases were then dried over magnesium sulphate and the solvent was subsequently stripped off in vacuo. 10 fractions of the above acid with a different E/Z ratio were thus obtained.

The E/Z ratio was determined by the ¹H-NMR spectrum.

Fraction I (acid separated off first) had an E/Z ratio of 85/15.

Fraction IX had an E/Z ratio of 40/60.

Fraction IX (10.4 g) was then dissolved in cyclohexane at 30°–40° C. By leaving the solution to stand at room temperature, (±)-trans-3-(Z-2-chloro-2-(4-chloro-phenyl)-vinyl)-2,2-dimethyl-cyclopropane-carboxylic acid crystallized out in the form of colorless crystals of melting point 141°–142° C. The structure was confirmed by the ¹H-NMR spectrum.

¹H-NMR spectrum in CDCl₃/TMS, τ (ppm): aromatic H: 2.37–2.81 (m/4 H), vinyl H: 4.10 (d/1 H), cyclopropane H: 7.26–7.56 (m/1 H) and 8.26 (d/1 H) and dimethyl H: 8.55 (s/3 H) and 8.70 (s/3 H).

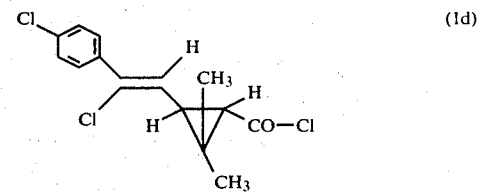

(1d)

1.0 g (0.0035 mol) of (±)-trans-3-(Z-2-chloro-2-(4-chloro-phenyl)-vinyl)-2,2-dimethyl-cyclopropanecarboxylic acid were dissolved in 20 ml of carbon tetrachloride, and 5 ml of thionyl chloride were added dropwise slowly at 25° C., while stirring. The mixture was then heated to the reflux temperature for 4 hours. After this reaction time, excess thionyl chloride and carbon tetrachloride were distilled off under a waterpump vacuum. Last residues of solvent were removed by brief incipient distillation at a bath temperature of 60° C./2 mm Hg. 1.03 g (96.9% of theory) of (±)-trans-3-(Z-2-chloro-2-(4-chloro-phenyl)-vinyl)-2,2-dimethyl-cyclopropanecarboxylic acid chloride were obtained as an oily liquid.

(e)

(1)

1.08 g (0.005 mol) of 3-phenoxy-4-fluoro-benzaldehyde and 1.52 g (0.005 mol) of (±)-trans-3-(Z-2-chloro-2-(4-chlorophenyl)-vinyl)-2,2-dimethyl-cyclopropanecarboxylic acid chloride were together added dropwise to a mixture of 0.4 g of sodium cyanide, 0.6 ml of water, 20 ml of n-hexane and 0.1 g of tetrabutylammonium bromide at 20°–25° C., whilst stirring, and the reaction mixture was then stirred at 20°–25° C. for 4 hours. 100 ml of toluene were subsequently added and the reaction mixture was extracted twice by shaking with 60 ml of water each time. The organic phases were separated off and dried over magnesium sulphate and the solvent was distilled off under a waterpump vacuum. Last residues of solvent were removed by brief incipient distillation at a bath temperature of 60° C./1 mm Hg. 1.8 g (70.6% of theory) of (±)-trans-3-(Z-2-chloro-2-(4-chlorophenyl)-vinyl)-2,2-dimethyl-cyclopropanecarboxylic acid (±)-α-cyano-3-phenoxy-4-fluoro-benzyl ester were obtained as a viscous oil. The structure was confirmed by the $^1$H-NMR spectrum.

$^1$H-NMR spectrum in CDCl$_3$/TMS, τ (ppm): aromatic H: 2.3–3.1 (m/12 H), benzyl H: 3.60 (s/1/2 H) and 3.62 (s/1/2 H), vinyl H: 4.14 (d/1 H), cyclopropane H: 7.26–7.57 (m/1 H) and 8.26 (d/1 H) and dimethyl H: 8.50–8.80 (m/6 H).

EXAMPLE 2

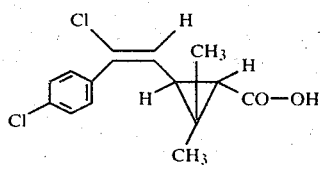
(a)

From Example 1(b) hereinabove 31.6 g (0.111 mol) of (±)-trans-(E/Z-2-chloro-2-(4-chloro-phenyl)-vinyl)-2,2-dimethyl-cyclopropanecarboxylic acid with an E/Z ratio of 60/40 were dissolved in 150 ml of methylene chloride and the solution was extracted by shaking with a solution of 0.885 g (0.222 mol) of sodium hydroxide in 50 ml of water. The aqueous phase was then separated off. This operation was then repeated a further 4 times. 5 fractions of an aqueous salt solution were thus obtained and each fraction by itself was then acidified with concentrated hydrochloric acid and subsequently extracted in each case with 2×50 ml of methylene chloride. The organic phases were separated off and dried over magnesium sulphate and the solvent was then stripped off in vacuo. 5 fractions of the above acid with a different E/Z ratio were thus obtained. The E/Z ratio was determined by the $^1$H-NMR spectrum.

Fraction I, that is to say the acid separated off first, has an E/Z ratio of 50/50.

Fraction V had an E/Z ratio of 87/13.

Fraction V (5 g) was then dissolved in cyclohexane at 30°–40° C. By leaving the solution to stand at room temperature, (±)-trans-3-(E-2-chloro-2-(4-chlorophenyl)-vinyl)-2,2-dimethyl-cyclopropane-carboxylic acid crystallized out in the form of colorless crystals of melting point 138°–139° C.

The structure was confirmed by the $^1$H-NMR spectrum.

$^1$H-NMR spectrum in CDCl$_3$/TMS, τ (ppm): aromatic H: 2.43–2.74 (m/4 H), vinyl H: 4.24 (d/1 H), cyclopropane H: 7.74–8.04 (m/1 H) and 8.39 (d/1 H) and dimethyl H: 8.73 (s/6 H).

The compound:

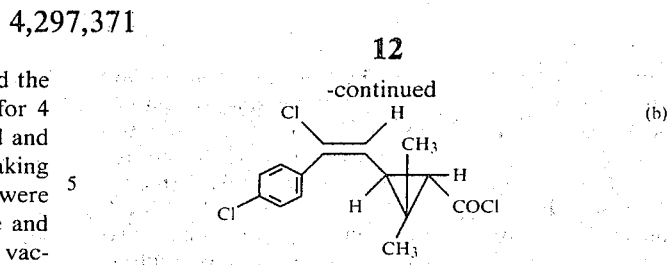
(b)

that is to say (±)-trans-3-(E-2-chloro-2-(4-chlorophenyl)-vinyl)-2,2-dimethyl-cyclopropanecarboxylic acid chloride, was obtained as an oily liquid from (±)-trans-3-(E-2-chloro-2-(4-chloro-phenyl)-vinyl)-2,2-dimethyl-cyclopropanecarboxylic acid and thionyl chloride, analogously to Example 1(c).

The compound

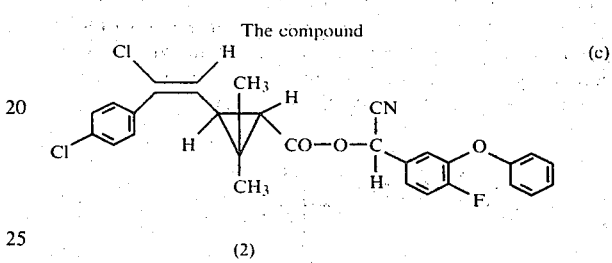
(c)

(2)

that is to say (±)-trans-3-(E-2-chloro-2-(4-chlorophenyl)-vinyl)-2,2-dimethyl-cyclopropanecarboxylic acid (±)-α-cyano-3-phenoxy-4-fluoro-benzyl ester, was obtained from 3-phenoxy-4-fluoro-benzaldehyde and (±)-trans-3-(E-2-chloro-2-(4-chloro-phenyl)-vinyl)-2,2-dimethyl-cyclopropanecarboxylic acid chloride analogously to Example 1.

$^1$H-NMR spectrum in CDCl$_3$TMS, τ (ppm): aromatic H: 2.3–3.1 (m/12 H), benzyl H: 3.70 (s/1/2 H) and 3.72 (s/1/2 H), vinyl H: 4.16–4.40 (m/1 H), cyclopropane H: 7.64–8.07 (m/1 H) and 8.39 (d/1 H) and dimethyl H: 8.57–8.92 (m/6 H).

EXAMPLE 3

The compound:

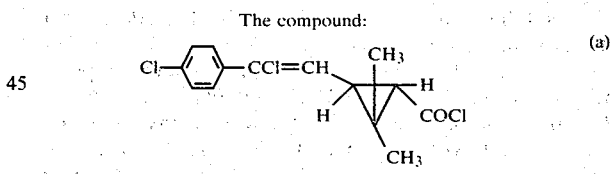
(a)

that is to say (±)-trans-3-(E/Z-2-chloro-2-(4-chlorophenyl)-vinyl)-2,2-dimethyl-cyclopropanecarboxylic acid chloride, was obtained as an oily liquid from (±)-trans-3-(E/Z-2-chloro-2-(4-chloro-phenyl)-vinyl)-2,2-dimethyl-cyclopropanecarboxylic acid and thionyl chloride, analogously to Example 1(c).

The compound

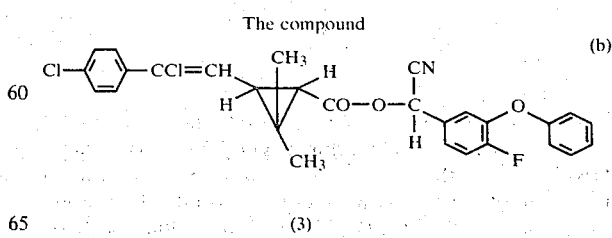
(b)

(3)

that is to say (±)-trans-3-(E/Z-2-chloro-2-(4-chlorophenyl)-vinyl)-2,2-dimethyl-cyclopropanecarboxylic acid (±)-α-cyano-3-phenoxy-4-fluoro-benzyl ester, was obtained from 3-phenoxy-4-fluoro-benzaldehyde and (±)-trans-3-(E/Z-2-chloro-2-(4-chloro-phenyl)-vinyl)-2,2-dimethyl-cyclopropanecarboxylic acid chloride analogously to Example 1.

¹H-NMR spectrum in CDCl₃/TMS, τ (ppm): aromatic H: 2.3–3.1 (m/12 H), vinyl H: 3.60–3.75 (m/1 H), vinyl H: 4.07–4.40 (m/1 H), cyclopropane H: 7.26–8.45 (m/2 H) and dimethyl H: 8.57–8.9 (m/6 H).

It will be understood that the specification and examples are illustrative but not limitative of the present invention and that other embodiments within the spirit and scope of the invention will suggest themselves to those skilled in the art.

We claim:

1. A substantially pure isomer mixture selected from the group consisting of (±)-trans-3-(E/Z-2-chloro-2-(4-chloro-phenyl)-vinyl)-2,2-dimethyl-cyclopropanecarboxylic acid (±)-2-cyano-3-phenoxy-4-fluoro-benzyl ester of the formula

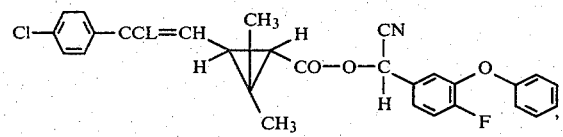

(±)-trans-3-(Z-2-chloro-2-(4-chloro-phenyl)-vinyl)-2,2-dimethyl-cyclopropanecarboxylic acid (±)-α-cyano-3-phenoxy-4-fluoro-benzyl ester of the formula

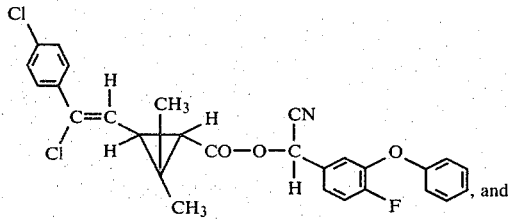
, and (±)-trans-3-(E-2-chloro-2-(4-chlorophenyl)-vinyl)-2,2-dimethyl-cyclopropanecarboxylic acid (±)-α-cyano-3-phenoxy-4-fluoro-benzyl ester of the formula

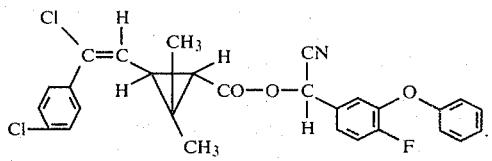

2. A mixture according to claim 1, wherein the mixture consists essentially of (±)-trans-3-(E/Z-2-chloro-2-(4-chloro-phenyl)-vinyl)-2,2-dimethyl-cyclopropanecarboxylic acid (±)-α-cyano-3-phenoxy-4-fluoro-benzyl ester.

3. A mixture according to claim 1, wherein the mixture consists essentially of (±)-trans-3-(Z-2-chloro-2-(4-chloro-phenyl)-vinyl)-2,2-dimethyl-cyclopropanecarboxylic acid (±)-α-cyano-3-phenoxy-4-fluoro-benzyl ester.

4. A mixture according to claim 1, wherein the mixture consists essentially of (±)-trans-3-(E-2-chloro-2-(4-chlorophenyl)-vinyl)-2,2-dimethyl-cyclopropanecarboxylic acid (±)-α-cyano-3-phenoxy-4-fluoro-benzyl ester.

5. An ectoparasiticidal composition of matter comprising an ectoparasiticidally effective amount of an isomer mixture according to claim 1.

6. A method of combating ectoparasites which comprises applying to such ectoparasites or to a habitat thereof an ectoparasiticidally effective amount of an isomer mixture according to claim 1.

7. The method according to claim 6, wherein the mixture consists essentially of (±)-trans-3-(E/Z-2-chloro-2-(4-chloro-phenyl)-vinyl)-2,2-dimethyl-cyclopropanecarboxylic acid (±)-α-cyano-3-phenoxy-4-fluoro-benzyl ester.

8. The method according to claim 6, wherein the mixture consists essentially of (±)-trans-3-(Z-2-chloro-2-(4-chloro-phenyl)-vinyl)-2,2-dimethyl-cyclopropanecarboxylic acid (±)-α-cyano-3-phenoxy-4-fluoro-benzyl ester.

9. The method according to claim 6, wherein the mixture consists essentially of (±)-trans-3-(E-2-chloro-2-(4-chlorophenyl)-vinyl-2,2-dimethyl-cyclopropanecarboxylic acid (±)-α-cyano-3-phenoxy-4-fluoro-benzyl ester.

10. An isomer mixture selected from the group consisting of a (±)-trans-3-(E/Z-, a (±)-trans-3-(Z- and a (±)-trans-3-(E-2-chloro-2-(4-chloro-phenyl)-vinyl)-2,2-dimethyl-cyclopropanecarboxylic acid or derivative thereof of the formula

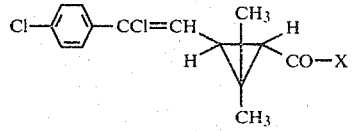

in which X is Cl, OH or C₁–C₄-alkoxy.

* * * * *